United States Patent
Ayala et al.

(10) Patent No.: US 8,702,625 B2
(45) Date of Patent: Apr. 22, 2014

(54) STEERABLE LOOP TIP WIRE-GUIDE

(75) Inventors: Juan Carlos Ayala, Santiago (CL); David M. Hardin, Winston-Salem, NC (US); Jason D. Foushee, Durham, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 662 days.

(21) Appl. No.: 11/234,990

(22) Filed: Sep. 26, 2005

(65) Prior Publication Data

US 2006/0100544 A1 May 11, 2006

Related U.S. Application Data

(60) Provisional application No. 60/614,908, filed on Sep. 30, 2004.

(51) Int. Cl.
*A61B 5/00* (2006.01)

(52) U.S. Cl.
USPC ............................................... 600/585

(58) Field of Classification Search
USPC ................... 600/433, 434, 585; 604/164.13
See application file for complete search history.

(56) References Cited

U.S. PATENT DOCUMENTS

| | | | | |
|---|---|---|---|---|
| 892,472 A * | 7/1908 | Walker | | 606/106 |
| 4,281,660 A | 8/1981 | Fujiwara | | 600/375 |
| 4,310,789 A | 1/1982 | Mank et al. | | 318/587 |
| 4,326,530 A * | 4/1982 | Fleury, Jr. | | 606/47 |
| 4,545,390 A | 10/1985 | Leary | | 600/462 |
| 4,800,890 A | 1/1989 | Cramer | | 600/434 |
| 5,037,391 A | 8/1991 | Hammerslag et al. | | 604/528 |
| 5,054,501 A | 10/1991 | Chuttani et al. | | 600/585 |
| 5,069,217 A | 12/1991 | Fleischhacker, Jr. | | 600/585 |
| 5,211,636 A | 5/1993 | MIsche | | 604/264 |
| 5,376,083 A | 12/1994 | Mische | | 604/264 |
| 5,387,219 A | 2/1995 | Rappe | | 606/108 |
| 5,433,200 A | 7/1995 | Fleischhacker, Jr. | | 600/434 |
| 5,490,845 A | 2/1996 | Racz | | 604/266 |
| 5,498,249 A | 3/1996 | Quinn | | 604/528 |
| 5,613,973 A | 3/1997 | Jackson et al. | | 606/113 |

(Continued)

FOREIGN PATENT DOCUMENTS

| | | |
|---|---|---|
| EP | 1 346 747 A | 9/2003 |
| JP | 07088191 | 4/1995 |
| WO | WO 2004/050161 A | 6/2004 |
| WO | WO 2004/089456 A | 10/2004 |

OTHER PUBLICATIONS

International Search Report dated Jan. 17, 2006 for corresponding International Application No. PCT/US2005/034280.

*Primary Examiner* — Max Hindenburg
*Assistant Examiner* — Jonathan M Foreman
(74) *Attorney, Agent, or Firm* — Brinks Gilson & Lione

(57) ABSTRACT

A steerable wire-guide comprises an elongate member having a longitudinal axis. The elongate member comprises a leading portion and a body portion. The leading portion comprises a loop and the body portion comprises a first wire and a second wire. The first and second wires are movable relative to each other such that relative movement of the first wire with respect to the second wire directs the leading portion in a first direction, which is at an angle relative to the longitudinal axis, and relative movement of the second wire with respect to the first wire directs the leading portion in a second direction different from the first direction.

1 Claim, 12 Drawing Sheets

(56) References Cited

U.S. PATENT DOCUMENTS

| | | | |
|---|---|---|---|
| 5,643,281 A | 7/1997 | Suhocki et al. | 606/113 |
| 5,728,122 A | 3/1998 | Leschinsky et al. | 606/213 |
| 5,730,704 A | 3/1998 | Avitall | 600/374 |
| 5,824,031 A | 10/1998 | Cookston et al. | 607/122 |
| 5,879,295 A * | 3/1999 | Li et al. | 600/373 |
| 5,904,648 A | 5/1999 | Arndt et al. | 600/120 |
| 6,056,743 A | 5/2000 | Ellis et al. | 606/15 |
| 6,102,918 A | 8/2000 | Kerr | 606/108 |
| 6,277,139 B1 | 8/2001 | Levinson et al. | 606/200 |
| 6,299,612 B1 * | 10/2001 | Ouchi | 606/47 |
| 6,371,970 B1 | 4/2002 | Khosravi et al. | 606/200 |
| 6,379,319 B1 | 4/2002 | Garibotto et al. | 600/585 |
| 6,425,895 B1 * | 7/2002 | Swanson et al. | 606/41 |
| 6,454,758 B1 | 9/2002 | Thompson et al. | 604/528 |
| 6,464,699 B1 | 10/2002 | Swanson | 606/41 |
| 6,620,179 B2 | 9/2003 | Boock et al. | 606/159 |
| 2002/0010426 A1 | 1/2002 | Clayman et al. | 604/170.01 |
| 2002/0016604 A1 | 2/2002 | Boock et al. | 606/159 |
| 2004/0016849 A1 | 1/2004 | Jakubowski et al. | 244/137.4 |
| 2004/0082881 A1 | 4/2004 | Grewe et al. | 600/585 |
| 2004/0106897 A1 | 6/2004 | Thompson et al. | 604/95.04 |
| 2004/0125139 A1 | 7/2004 | Beck et al. | 345/764 |
| 2004/0193032 A1 | 9/2004 | Mogul | 600/374 |
| 2004/0193205 A1 | 9/2004 | Burgermeister | 606/194 |
| 2004/0199088 A1 * | 10/2004 | Bakos et al. | 600/585 |
| 2004/0215208 A1 | 10/2004 | Foushee et al. | 606/108 |
| 2005/0027243 A1 | 2/2005 | Gibson et al. | 604/95.04 |
| 2005/0038412 A1 | 2/2005 | Rabiner et al. | 604/528 |
| 2005/0043779 A1 | 2/2005 | Wilson | 623/1.11 |
| 2005/0080356 A1 | 4/2005 | Dapolito et al. | 600/585 |
| 2005/0096590 A1 | 5/2005 | Gullickson et al. | 604/95.04 |
| 2006/0100544 A1 | 5/2006 | Ayala et al. | 600/585 |

* cited by examiner

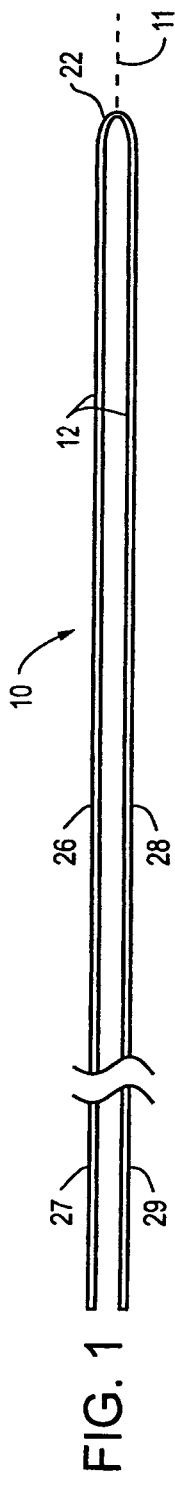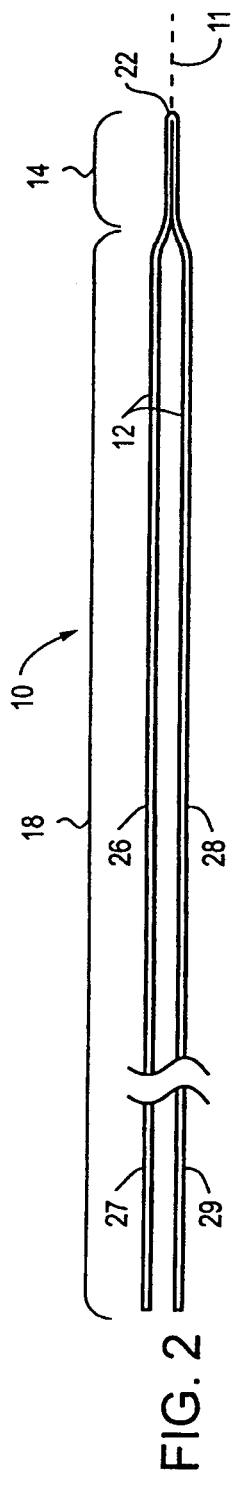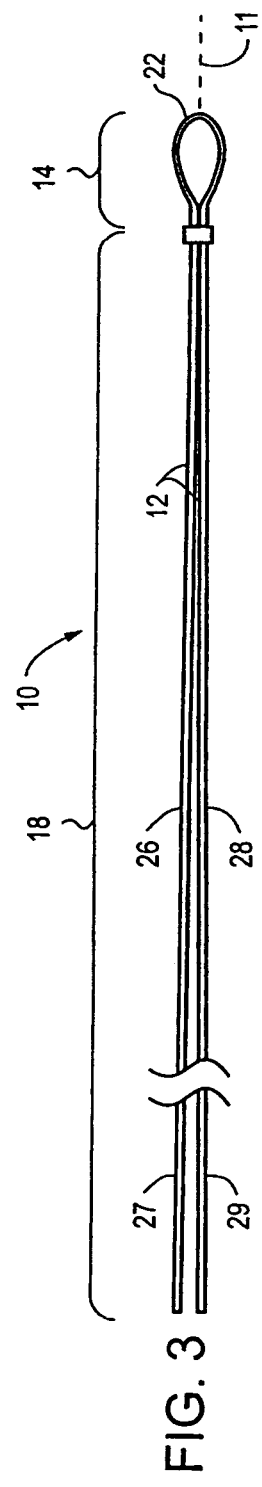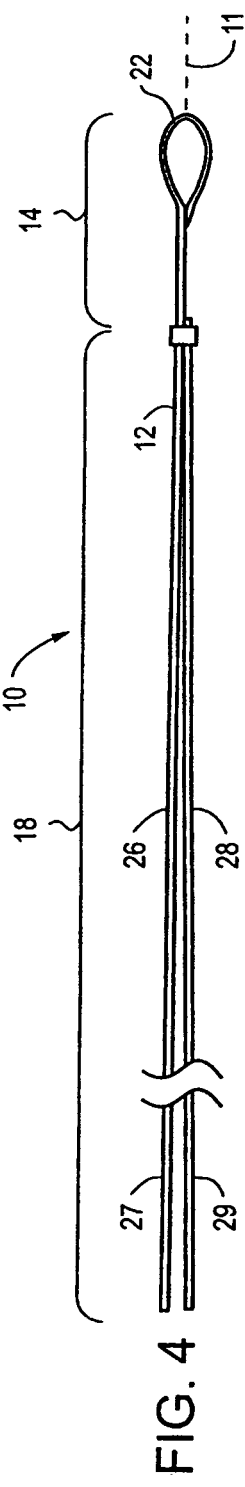

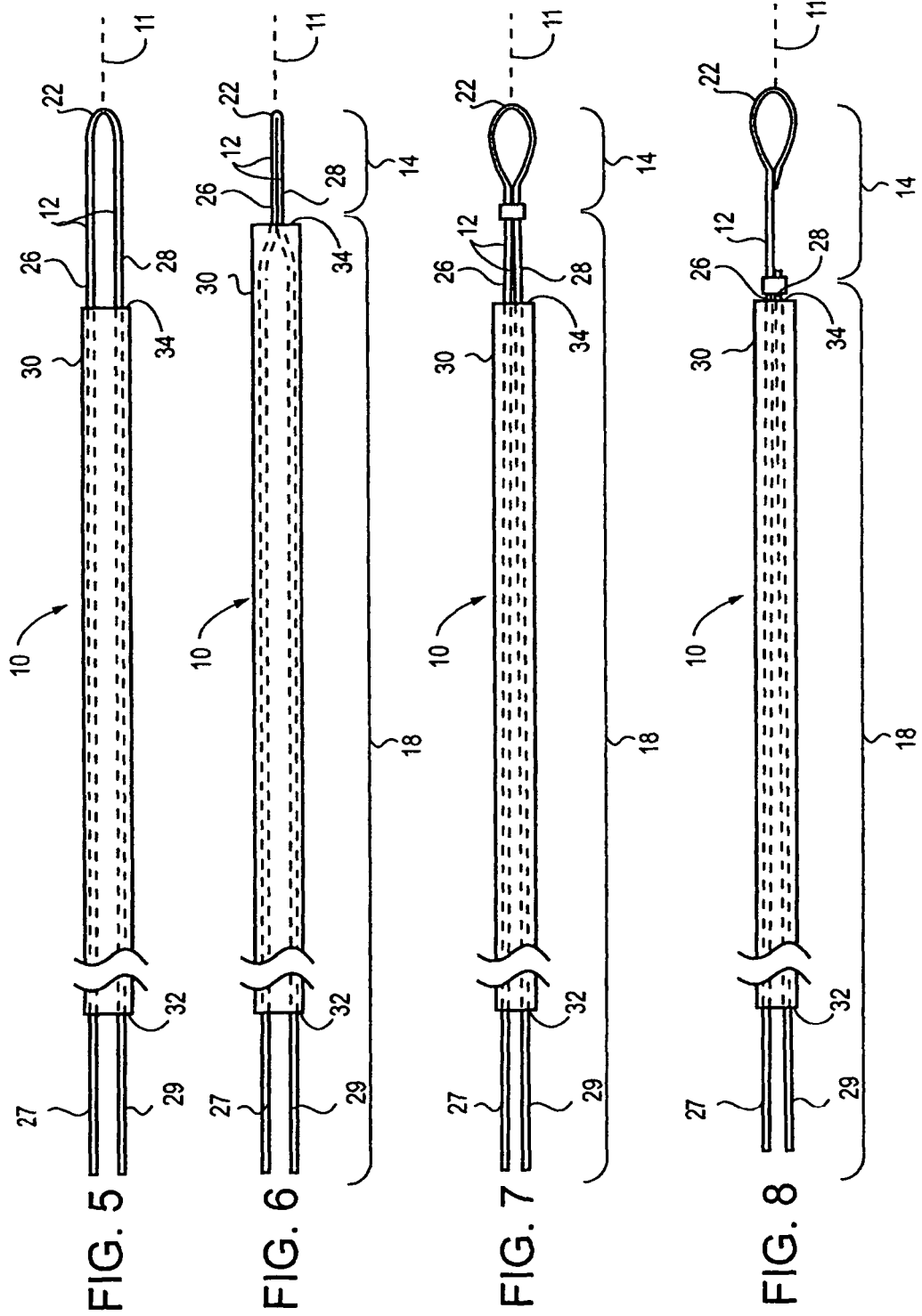

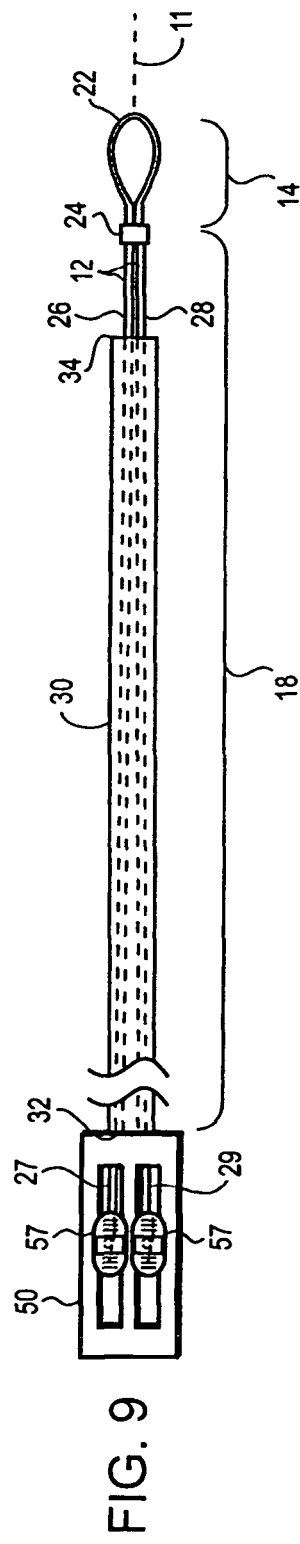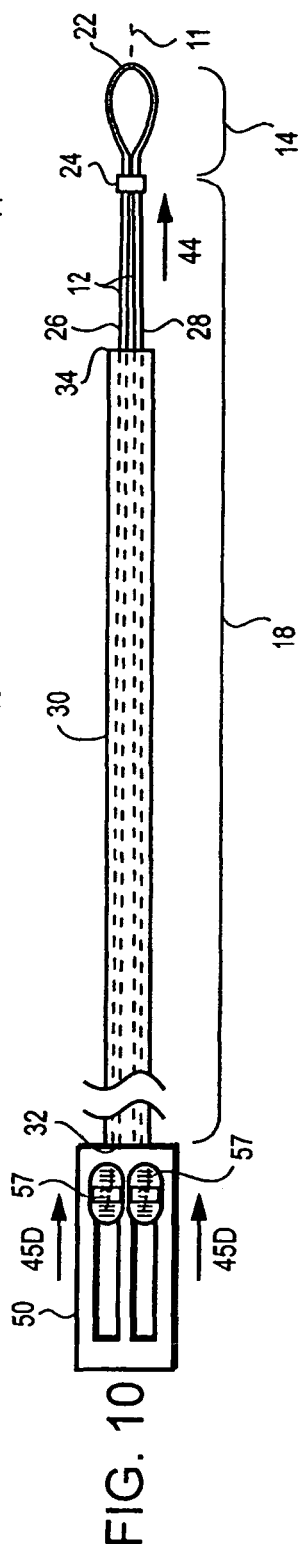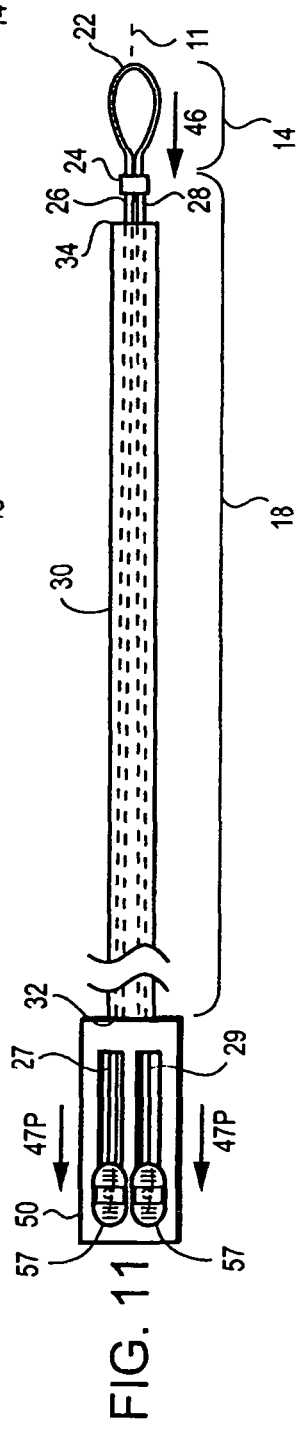

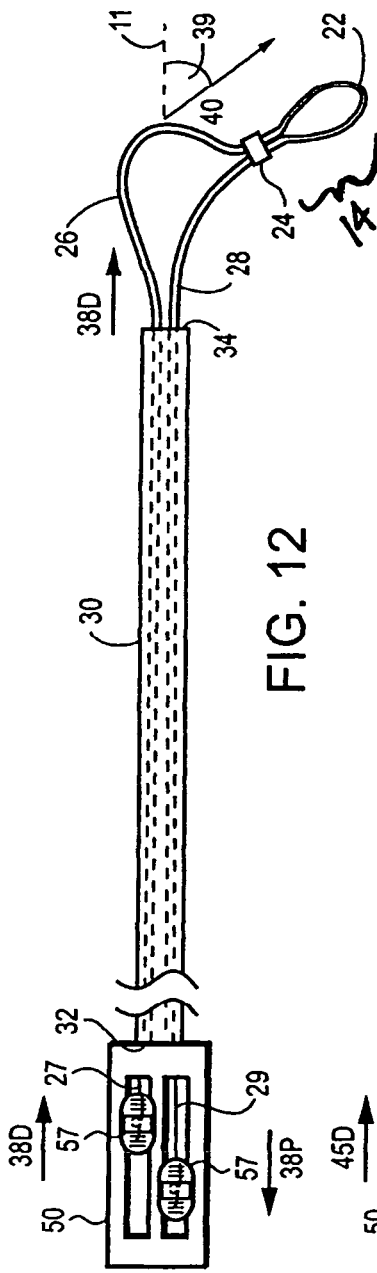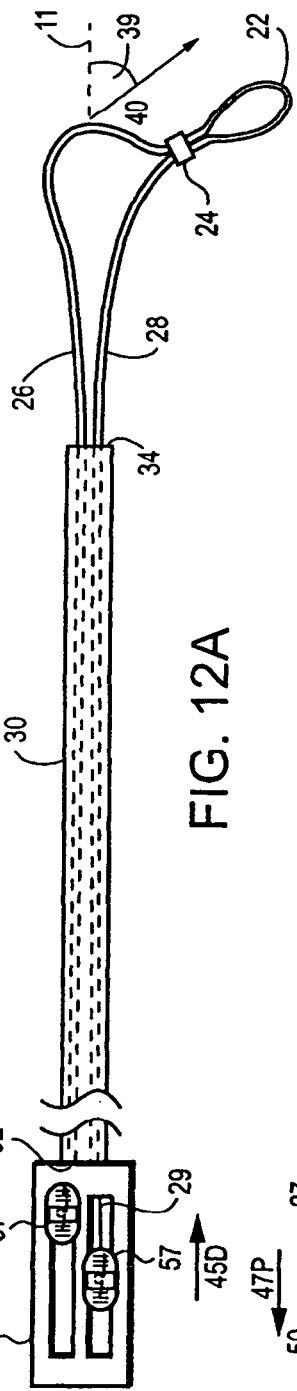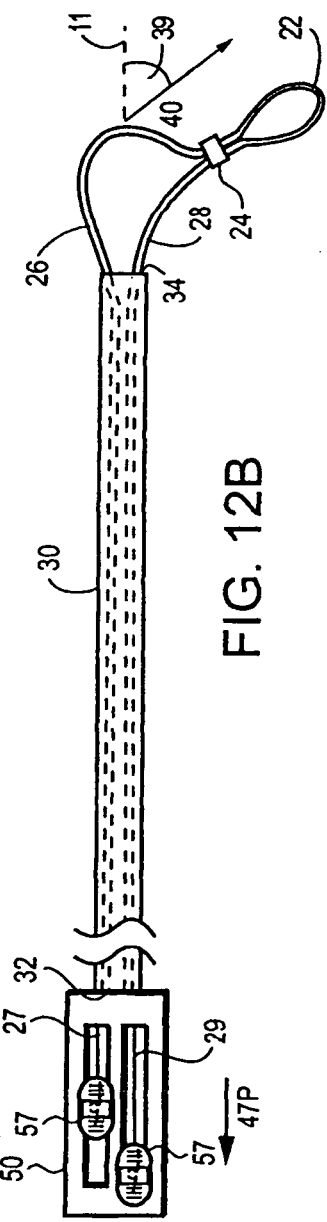

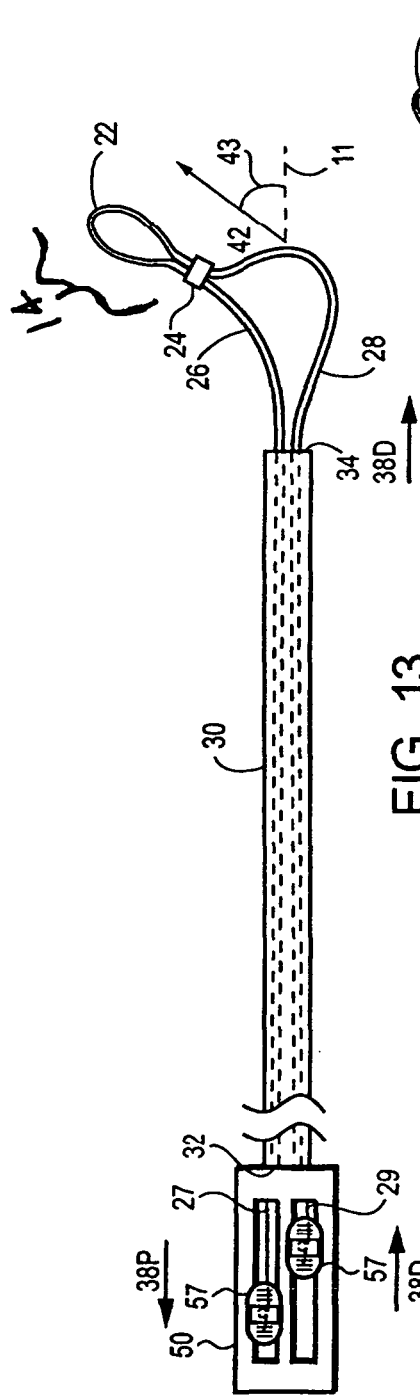
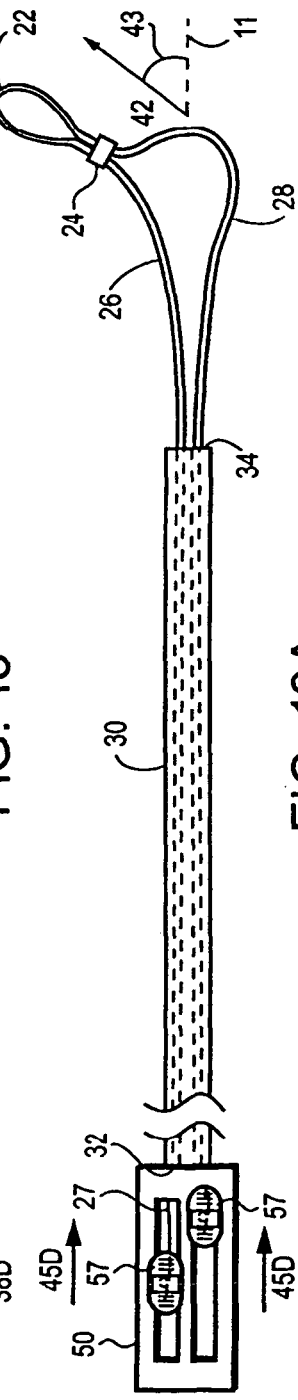
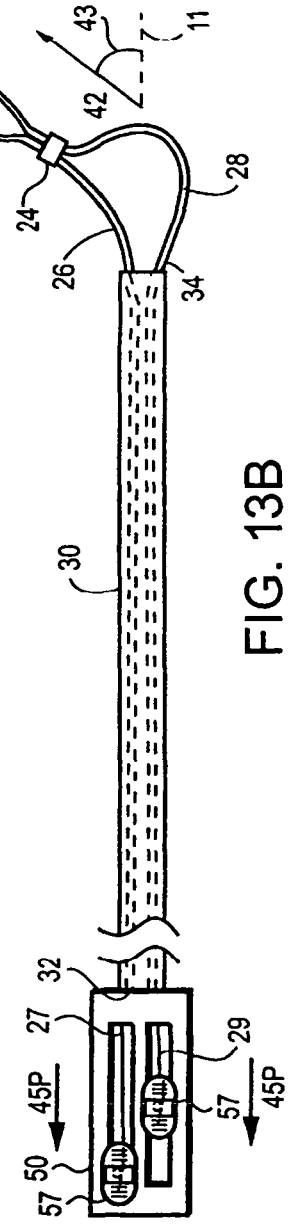
FIG. 13
FIG. 13A
FIG. 13B

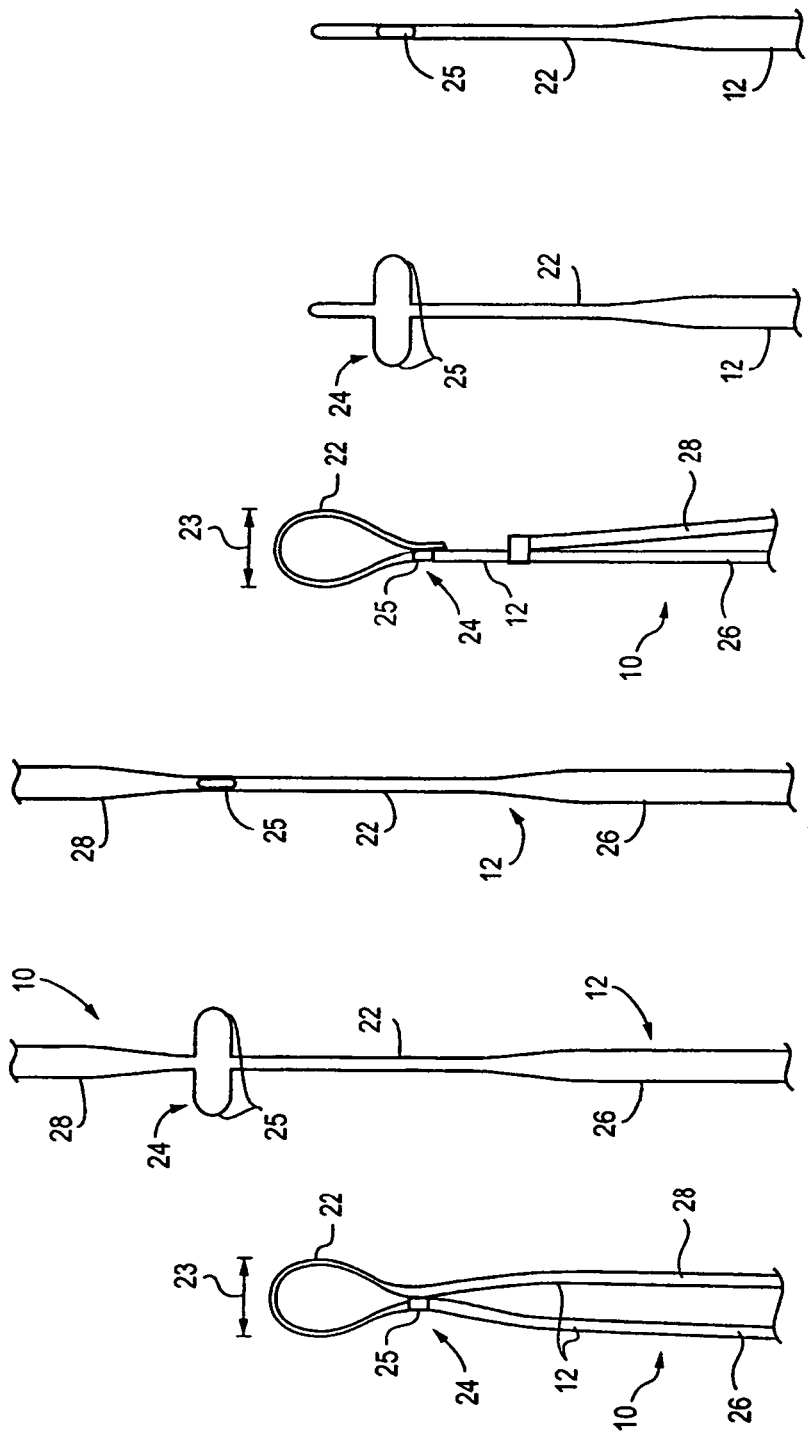

STEERABLE LOOP TIP WIRE-GUIDE

RELATED APPLICATIONS

This application claims the benefit of priority from U.S. Provisional Application No. 60/614,908, filed Sep. 30, 2004, which is incorporated herein by reference.

FIELD OF THE INVENTION

The present invention relates to wire-guides used in the placement of medical devices. More specifically, the present invention relates to a steerable wire-guide having a loop tip.

BACKGROUND OF THE INVENTION

Wire-guides are elongate flexible members used to provide a path along which another medical device can be moved. The path provided by the wire-guide can be used to navigate another medical device, such as a catheter, through a body vessel. The use of wire-guides to define such a path is known in the art. Briefly, a wire-guide is navigated through a body vessel toward a point of treatment. Once positioned within the vessel, a second medical device, frequently a cannula such as a catheter is placed over the wire-guide and moved along its length toward the point of treatment. Thus, the wire-guide provides an established path for placing other devices, eliminating the need for performing delicate navigation procedures for each device passed into the vessel.

During placement of a wire-guide, an operator must navigate the wire-guide through the vessel(s). Often, the vessel defines a torturous path due to the presence of natural bends and/or curves, or unnatural impediments, such as tumors, build-ups, and/or strictures. The presence of a torturous path may make navigation of a wire-guide difficult. For example, the presence of an impediment may block the wire-guide from navigating further into the vessel.

The prior art contains many examples of wire-guides having straight flexible tips intended to aid in the navigation around such impediment. The presence of a straight flexible tip, however, may in fact make navigation more difficult. For example, upon encountering an impediment, the straight flexible tip may bend toward one of the vessel walls. Further, the straight tip may bend and turn back upon itself upon encountering the impediment. This formation of an unstable turn in the wire-guide makes further navigation difficult.

One successful device developed to address this need in the art is the loop tip wire-guide disclosed in pending U.S. application Ser. No. 10/719,764, entitled "Loop Tip Wire-guide," filed Nov. 21, 2003, which claims priority to U.S. Provisional Application Ser. No. 60/430,466, filed Dec. 2, 2002, each of which are incorporated by reference. In this device, a resilient loop positions, and a closure member affixes, the distal end of a wire-guide relative to the wire-guide. When this device is navigated through a body vessel and encounters an impediment, the distal end of the wire-guide does not move relative to the remainder of the wire-guide due to the presence of the loop and closure member. Instead, the loop deforms in response to the impediment. The resiliency of the loop creates a force opposing the impediment and directs the loop away from the impediment. This defines a path for the remainder of the wire-guide to follow and enables the wire-guide to navigate about the impediment and continue along the interior of the vessel.

Yet, additional improved embodiments of a loop tip wire-guide are desirable. For example, the point of treatment may be located in a side branch or beyond a bifurcation of the main vessel. It would be desirable if a loop tip wire-guide provided the user with the greater ability to direct the loop tip of the wire-guide through a main body vessel and into a branch vessel or a bifurcation. For this reason, a steerable wire-guide would be desirable.

BRIEF SUMMARY OF THE INVENTION

The present invention provides a steerable wire-guide having a loop. In one embodiment, the invention is a steerable wire-guide comprising a longitudinal axis and an elongate member. The elongate member has a leading portion and a body portion. The leading portion comprises a loop and the body portion comprises a first wire and a second wire. The first and second wires are movable relative to each other such that relative distal movement of the first wire with respect to the second wire directs the leading portion in a first direction, which is at an angle relative to the longitudinal axis, and relative distal movement of the second wire with respect to the first wire directs the leading portion in a second direction different from the first direction.

In another embodiment, the invention is a steerable wire-guide comprising a longitudinal axis, a tubular member and an elongate member. The tubular member comprises a tubular member proximal end and a tubular member distal end. The elongate member comprises a leading portion and a body portion. The elongate member is slidably disposed and oriented within the tubular member such that the leading portion extends from the tubular member distal end. The leading portion comprises a loop and the body portion comprising a first wire and a second wire. The first and second wires being movable such that: relative distal movement of the first wire with respect to the second wire directs the leading portion in a first direction at an angle relative to the longitudinal axis; relative distal movement of the second wire with respect to the first wire directs the leading portion in a second direction different from the first direction; concurrent distal movement of the first and second wires advances the leading portion distally; and concurrent proximal movement of the first and second wires retracts the leading portion proximally.

In an alternate embodiment, the invention is a steerable wire-guide comprising: a longitudinal axis, a tubular member, an elongate member and a removable handle. The tubular member comprises a tubular member proximal end and a tubular member distal end. The elongate member comprises a leading portion and a body portion. The leading portion comprises a loop and the body portion comprising a first wire and a second wire. The first wire comprises a first wire proximal end-portion and the second wire comprises a second wire proximal end-portion. The elongate member is slidably disposed and oriented within the tubular member such that the leading portion extends from the tubular member distal end and the first wire proximal end-portion and the second wire proximal end-portion extend from the tubular member proximal end. The first and second wires are movable such that: relative distal movement of the first wire with respect to the second wire directs the leading portion in a first direction at an angle to the longitudinal axis; relative distal movement of the second wire with respect to the first wire directs the leading portion in a second direction different from the first direction; concurrent distal movement of the first and second wires advances the leading portion distally; and concurrent proximal movement of the first and second wires retracts the leading portion proximally. The removable handle is attached to the tubular member proximal end and the first wire proximal end-portion and the second wire proximal end-portion are mounted for movement on the removable handle. The removable handle comprises a releasable locking mechanism for selectively affixing the first wire proximal end-portion and the second wire proximal end-portion relative to each other.

In yet other alternate embodiments, the steerable wire-guide can have any one or more of the following: a closure member closing the loop, a radiopaque marker on the closure member and/or the elongate member. Optionally, a covering is positioned over the closure member and/or at least a portion of the elongate member.

BRIEF DESCRIPTION OF THE DRAWINGS

The present invention will be more fully appreciated as the same becomes better understood from the following detailed description when considered in connection with the accompanying drawings, in which like reference numerals and characters designate like or corresponding parts through the several views.

FIG. 1 is a side-view of a steerable wire-guide according to an embodiment of the invention.

FIG. 2 is a side-view of a steerable wire-guide according to an alternate embodiment of the invention.

FIG. 3 is a side-view of a steerable wire-guide according to an alternate embodiment of the invention.

FIG. 4 is a side-view of a steerable wire-guide according to an alternate embodiment of the invention.

FIG. 5 is a side-view of a steerable wire-guide according to an alternate embodiment of the invention.

FIG. 6 is a side-view of a steerable wire-guide according to an alternate embodiment of the invention.

FIG. 7 is a side-view of a steerable wire-guide according to an alternate embodiment of the invention.

FIG. 8 is a side-view of a steerable wire-guide according to an alternate embodiment of the invention.

FIG. 9 is a side-view of a steerable wire-guide according to an alternate embodiment of the invention.

FIG. 10 is a side-view of the steerable wire-guide of FIG. 9 showing the first and second wires concurrently moving distally and the leading portion advancing.

FIG. 11 is a side-view of the steerable wire-guide of FIG. 9 showing the first and second wires concurrently moving proximally and the leading portion retracting.

FIG. 12 is a side-view of the steerable wire-guide of FIG. 9 illustrating the first wire moving distally relative to the second wire and the leading portion bending in a first direction that is at an angle to the longitudinal axis.

FIG. 12A is a side-view of the steerable wire-guide of FIG. 12 illustrating the first and second wires concurrently moving distally and leading portion advancing in the first direction.

FIG. 12B is a side-view of the steerable wire-guide of FIG. 12 illustrating the first and second wires concurrently moving proximally and the leading portion retracting in the first direction.

FIG. 13 is a side-view of the steerable wire-guide of FIG. 9 illustrating the second wire moving distally relative to the first wire and the leading portion bending in a second direction that is at an angle to the longitudinal axis and is different from the first direction.

FIG. 13A is a side-view of the steerable wire-guide of FIG. 13 illustrating the first and second wires concurrently moving distally and the leading portion advancing in the second direction.

FIG. 13B is a side-view is a side-view of the steerable wire-guide of FIG. 13 illustrating the first and second wires concurrently moving proximally and the leading portion retracting in the second direction.

FIG. 23 is a side-view of a steerable wire-guide according to an alternate embodiment of the invention.

FIG. 23A is a top-view of the steerable wire-guide of FIG. 23 in an unassembled form illustrating an alternate embodiment of a closure member.

FIG. 23B is a side-view of the steerable wire-guide of FIG. 23A.

FIG. 28 is a side-view of the steerable wire-guide of FIG. 4 illustrating an alternate embodiment of a closure member.

FIG. 28A is a top-view of the steerable wire-guide of FIG. 28 in an unassembled form illustrating an alternate embodiment of a closure member.

FIG. 28B is a side-view of the steerable wire-guide of FIG. 28A.

DETAILED DESCRIPTION OF THE INVENTION

Figure 15:
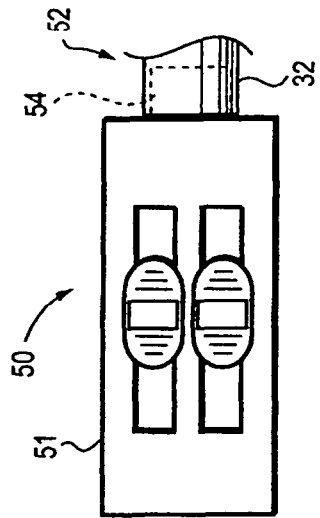
FIG. 15 is a side-view of a releasable connector detachably connecting a gripping portion of a removable handle and a tubular member proximal end according to an alternate embodiment of the invention.

Turning now to the drawings, wherein like numerals indicate the same element throughout the views, there is shown in FIGS. 1-33 a steerable wire-guide 10 made in accordance with the present invention. Steerable wire-guide 10 enables the user to direct, or steer, the steerable wire-guide 10 through a body lumen. Steerable wire-guide 10 comprises a longitudinal axis 11 and an elongate member 12 having a leading portion 14 and a body portion 18. The leading portion 14 comprises a loop 22 and the body portion 18 comprises a first wire 26 and a second wire 28.

Any method of forming loop 22 is contemplated. In the embodiments shown in the figures, the elongate member 12 defines the loop 22. More particularly, the loop 22 comprises a section of the elongate member 12 bent back upon itself. The loop 22 can be formed anywhere along the length of the elongate member 12. For example, FIGS. 1-3, 5-7, 9-13, 18-23B, 30 and 33 show the loop 22 formed at about the mid-portion of the elongate member 12. In these embodiments, the elongate member 12 is bent at about its mid-portion to form the loop 22 of the leading portion 14. The two juxtaposed portions of the elongate member 12 form the first and second wires 26, 28, respectively, of the body portion 18.

By way of other non-limiting examples, FIGS. 4, 8, 24-29 and 31-32 show loop 22 formed at an end-portion of the elongate member 12. In these embodiments, the loop 22 is formed by bending an end-portion of the elongate member 12 and attaching an end 13 to the end-portion to form the loop 22 of the leading portion 14. The portion of the elongate member 12 proximal to the loop 22 comprises the first wire 26 of the body portion 18. An additional wire is attached to the first wire 26 proximal to the leading portion 14 to form the second wire 28 of the body portion 18. The second wire 28 can be attached by using bonds (including solder bonds, welded bonds or molded bonds), adhesives, separate members (such as sutures or other appropriate tying members, cannulas or other connectors) or laser cutting techniques as are known in the art. Alternatively, the second wire 28 can be attached to the first wire 26 by twisting a portion of the additional wire about a portion of the first wire 26. The terms "proximal" and "distal" refer to the position "closest" and "furthest" to the user of the steerable wire-guide, respectively.

As an alternative to forming the loop 22 from the elongate member 12, a separate member defining the loop 22 can be affixed to two substantially straight wires to form the steerable wire-guide of the present invention (not shown). This may be advantageous when it is desirable to form the loop and elongate member of different materials. For example, a nylon or silicon loop could be formed and attached, such as by a closure member, to an elongate member formed of Nitinol™.

Figure 22:
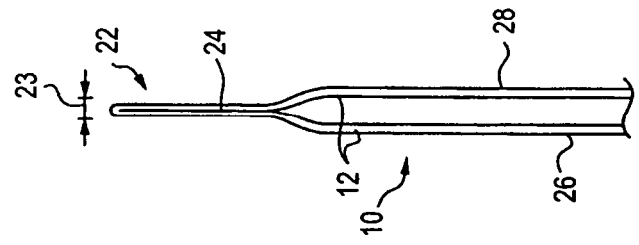
FIG. 22 is a side-view of a steerable wire-guide of FIG. 2 illustrating an alternate embodiment of a closure member.
Figure 21:
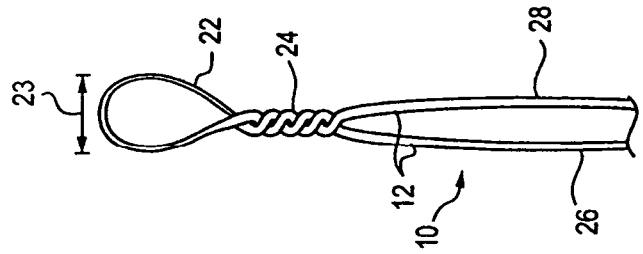
FIG. 21 is a side-view of a steerable wire-guide of FIG. 3 illustrating an alternate embodiment of a closure member.
Figure 20:
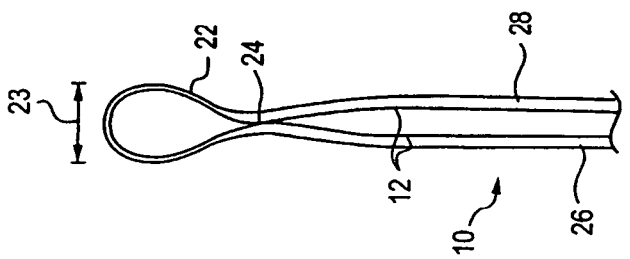
FIG. 20 is a side-view of a steerable wire-guide of FIG. 3 illustrating an alternate embodiment of a closure member.
Figure 19:
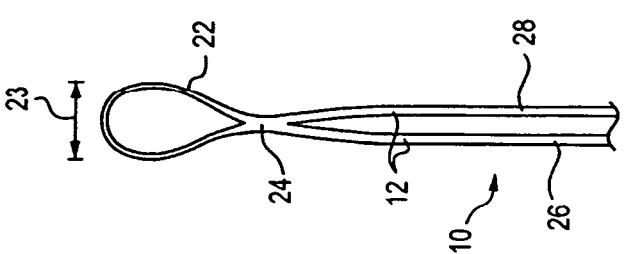
FIG. 19 is a side-view of a steerable wire-guide of FIG. 3 illustrating an alternate embodiment of a closure member.
Figure 29:
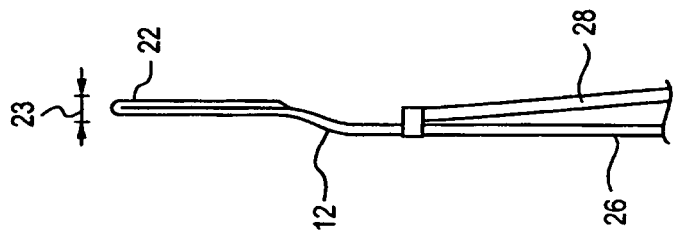
FIG. 29 is a side-view of the steerable wire-guide of FIG. 4 illustrating an alternate embodiment of a closure member.
Figure 27:
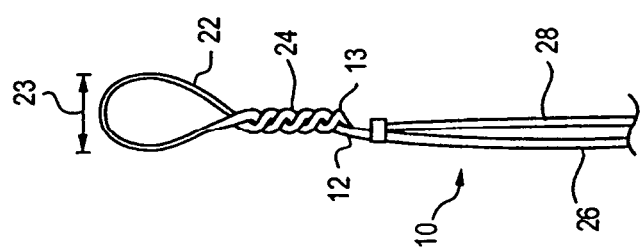
FIG. 27 is a side-view of the steerable wire-guide of FIG. 4 illustrating an alternate embodiment of a closure member.
Figure 26:
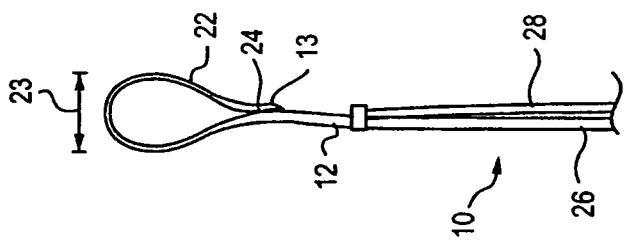
FIG. 26 is a side-view of the steerable wire-guide of FIG. 4 illustrating an alternate embodiment of a closure member.
Figure 25:
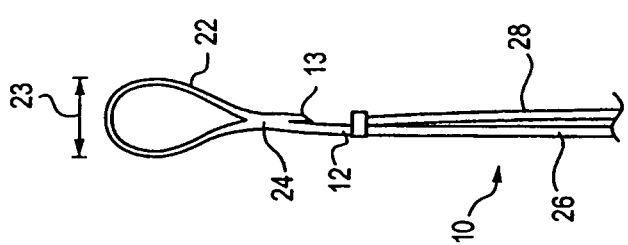
FIG. 25 is a side-view of the steerable wire-guide of FIG. 4 illustrating an alternate embodiment of a closure member.

Loop 22 can comprise any suitable shape including, but not limited to, circular, elliptical or ovoid. For example, FIGS. 3-4, and 7-13, 18-21 and 23-28 show the loop 22 comprises a curvilinear loop forming a generally ovoid shape. By way of another non-limiting example, FIGS. 1-2, 5-6, 22 and 29 show the loop 22 comprises a generally elliptical shape. Loop 22 further comprises a loop width 23 as shown in FIGS. 18-22 and 24-29. Loop width 23 can be greater than (as shown in FIGS. 18-21 and 24-27), about the same as (see FIGS. 1 and 5), or less than (as shown in FIGS. 22 and 29) the diameter of the body portion 18. The term 'loop width' refers to the distance between the two outer most surfaces of the elongate member 12 at the widest portion of the loop 22.

Figure 18:
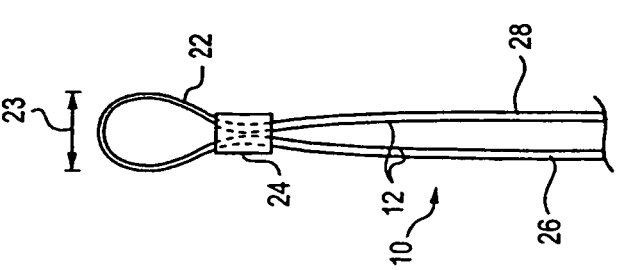
FIG. 18 is a side-view of the steerable wire-guide of FIG. 3 showing an embodiment of a closure member.
Figure 24:
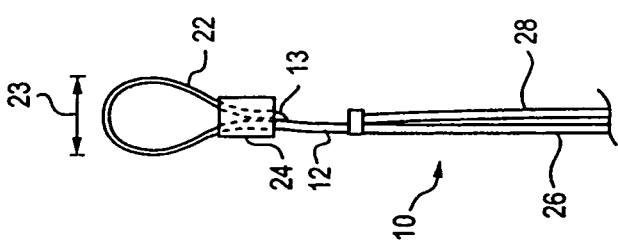
FIG. 24 is a side-view of the steerable wire-guide of FIG. 4 illustrating an alternate embodiment of a closure member.

Optionally, the steerable wire-guide 10 comprises a closure member 24 to close the loop 22 as shown in FIGS. 18-28. Alternatively, steerable wire-guide 10 may be formed without closure member 24 as shown in FIGS. 1 and 4. The closure member 24 closes the loop 22 such that no opening exists to the interior space of the loop 22 as shown in FIGS. 18-28. Any suitable closure member can be used, including bonds, adhesives, and separate members. Examples of suitable closure members include sutures or other appropriate material tying the two sections together, adhesive bonds and other bonds (such as a solder bond, a welded bond, or a molded bond) and a connector (such as a rivet). As best illustrated in FIGS. 18 and 24, the closure member 24 is a cannula defining an interior lumen. Two sections of the elongate member 12 are positioned within the cannula to form the loop 22. The closure member 24 is tightened, such as by crimping, to fix the loop 22 in overall size. In the alternate embodiments shown in FIGS. 19 and 25 the closure member 24 is a molded bond. The loop 22 of wire-guide 10 is formed by molding two sections of the elongate member together. In other alternate embodiments shown in FIGS. 20, 22 and 26 the closure member 24 is a welded bond. Two sections of the elongate member are welded or soldered together to form loop 22. In the alternate embodiments shown in FIGS. 21 and 27 the closure member 24 is coiled wire. More specifically, the loop 22 of steerable wire-guide 10 is formed from two sections of the elongate member wound about each other. In yet other another alternate embodiment (not shown), the closure member 24 is integral with the elongate member 12. In this case, the loop 22 and the elongate member 12 of steerable wire-guide 10 are formed using laser cutting techniques as are known to those skilled in the art. In still another alternate embodiment shown in FIGS. 23-23B and 28-28B, the closure member 24 comprises attachment tabs 25 which are bent about a portion of the elongate member 12.

Optionally, the diameter of the material used to form the loop 22 may be less than the diameter of the material that forms the body portion 18. For example, as best seen in FIGS. 23-23B and 28-28B, the diameter of the elongate member 12 that comprises the loop 22 may be less than the diameter of the elongate member that forms the first and second wires 26, 28 of the body portion 18.

The closure member 24 can be formed of any suitable material, and need only be biocompatible and capable of maintaining the loop 22 in a closed position. Preferably, the closure member 24 comprises a cannula formed of stainless steel or a shape memory material, such as Nitinol™. Also preferable, the closure member 24 is able to maintain a tightened position on the elongate member 12 upon application of a suitable force, such as by applying a crimping workload to the closure member 24.

As shown in the figures, the body portion 18 of the elongate member 12 comprises a first wire 26 and a second wire 28. The first wire 26 and the second wire 28 are movable relative to one another and concurrently. By manipulating the first and second wires 26, 28, the user is able to steer the steerable wire-guide 10 from a main lumen into a branch lumen or bifurcation, or about a curve or impediment. In general, relative movement of the first and second wires 26, 28, bends, or directs, the leading portion 14 of the steerable wire-guide 10 at an angle relative to the longitudinal axis 11 as shown in FIGS. 12-13B. Starting from a configuration with the first and second wires 26, 28 generally aligned (as shown in FIG. 11), relative distal movement of the first wire 26 with respect to the second wire 28 (indicated by arrow 38D in FIG. 12) directs the leading portion 14 in a first direction 40, which is defined by an angle 39 relative to the longitudinal axis 11. Alternatively, the first direction 40 can also be attained by relative proximal movement of the second wire 28 (indicated by arrow 38P in FIG. 12) with respect to the first wire 26. Turning to FIG. 13, relative distal movement of the second wire 28 (indicated by arrow 38D) with respect to the first wire 26 directs the leading portion 14 in a second direction 42, which is defined by an angle 43 relative to the longitudinal axis 11. The leading portion 14 may also be oriented into the second direction 42 by proximally moving the first wire 26 relative to the second wire 28 (indicated by arrow 38P).

The angle at which the leading portion bends may be related to the distance the first and second wires are moved relative to their generally aligned configuration. Thus, when the first and second wires 26, 28 are generally aligned, as shown in FIG. 9, the leading portion 14 is substantially parallel to the longitudinal axis 11. FIG. 12 indicates that as the first wire 26 is moved distally from its generally aligned configuration, the angle 39 at which the leading portion 14 bends in the first direction 40 increases. Also, as the second wire 28 moves proximally from its generally aligned configuration, the angle 39 at which the leading portion 14 bends in the first direction 40 increases. As FIGS. 13, 13A, and 13B indicate, as the second wire 28 is moved distally (or the first wire 26 is moved proximally) from its generally aligned configuration, the angle 43 at which the leading portion 14 bends in the second direction 42 increases. Depending on the distance that at least one of the first and second wires 26, 28 is moved from its generally aligned configuration, the leading portion 14 can be bent from a substantially parallel configuration to a slightly bent configuration to a perpendicular configuration and can be further bent back onto itself.

The leading portion 14 may be returned to a substantially parallel position with respect to the longitudinal axis 11 by substantially aligning the first and second wires 26, 28. Referring to FIG. 12 where the first wire 26 is distal to the second wire 28 and the leading portion 14 is bent in the first direction 40, the leading portion 14 can be returned to a substantially parallel position by either moving the first wire 26 proximally or moving the second wire 28 distally to substantially align the first and second wires 26, 28. Similarly, turning to FIG. 13 where the second wire 28 is distal to the first wire 26 and the leading portion 14 is bent in a second direction 42, the leading portion 14 can be returned to a substantially parallel position by either moving the second wire 28 proximally or moving the first wire 26 distally until the first and second wires 26, 28 are substantially aligned.

In general, concurrent distal movement of the first and second wires 26, 28 advances the leading portion 14 of the steerable wire-guide 10, whereas concurrent proximal movement retracts the leading portion 14 of the steerable wire-guide 10. FIGS. 9-11 illustrate the maneuverability of the leading portion 14 of the steerable wire-guide 10 in the circumstance where the first and second portions 26, 28 are concurrently moved in a generally aligned configuration. Thus, FIG. 10 illustrates the leading portion 14 advancing distally in a third direction 44 as the first and second wires 26, 28 are concurrently pushed in the distal direction (indicated by arrows 45D), and FIG. 11 shows leading portion 14 retracting proximally in a fourth direction 46 as the first and second wires 26, 28 are concurrently pulled in the proximal direction (indicated by arrows 47P). Due to the concurrent movement and the general alignment of the first and second wires 24, 26, the third and fourth directions 44, 46 are substantially parallel to the longitudinal axis 11. In this manner the steerable wire-guide 10 can be advanced through, or retracted from, the relatively straight portions of a body lumen.

In the case where at least one of the first and second wires 26, 28 has been moved from a substantially aligned configuration, the maneuverability of the leading portion 14 as the first and second wires 26, 28 are concurrently moved is illustrated in FIGS. 12-12B and 13-13B. In these cases, due to the relative movement of at least one of the first and second wires 26, 28 from its aligned configuration (shown in FIGS. 12 and 13), the leading portion 14 can be advanced and retracted in the bent configuration defined by the angles 39, 43 with respect to the longitudinal axis 11. Thus, FIG. 12A shows that concurrent distal movement of the first and second wires 26, 28 (indicated by arrows 45D) advances the leading portion 14 in the first direction 40 at an angle 39. FIG. 12B shows that concurrent proximal movement of the first and second wires 26, 28 (indicated by arrows 47P) retracts the leading portion 14 from the first direction 40. Similarly, FIG. 13A shows that concurrent distal movement of the first and second wires 26, 28 (indicated by arrows 45D) advances the leading portion 14 in the second direction 42 at an angle 43, whereas concurrent proximal movement of the first and second wires 26, 28 (indicated by arrows 47P) retracts the leading portion 14 from the second direction 42, as shown in FIG. 13B. In this manner, the steerable wire-guide 10 can be advanced through the curved portions of a main body lumen and into a branch lumen or a bifurcation and retracted therefrom.

Any suitable material can be used for the elongate member 12, and a variety of suitable materials are known to those skilled in the art. The material chosen may be biocompatible and capable of being formed into the structures described herein. Examples of suitable materials include stainless steel, Nitinol™ and other nickel-titanium alloys, MP35N® and other nickel-cobalt alloys, Cobalt L-605™ and other cobalt-chromium alloys, other biocompatible metals, and metal-alloys, as well as polymeric materials. The elongate member 12 can comprise a wire, a tubular member, a coil spring or a sheet of material. Further, the elongate member 12 can be formed of a series of layers, or as a coated core structure. For example, the elongate member 12 can comprise Nitinol™ with a solid core in one embodiment or a Nitinol™ core with a polytetrafluoroethylene covering in another embodiment.

A variety of shapes and sizes of elongate members and loops can be used, and these can both be optimized based on particular applications. The dimensions of the elongate member 12 and loop 22 will depend upon various factors, including the intended use of the wire-guide and the vessels into which the wire-guide will be positioned. By way of a non-limiting example, a steerable wire-guide that is intended to cannulate the common bile duct may include a combined diameter of the first and second wires, which are configured side-by-side, between about 0.016 inches and about 0.038 inches. Optionally, the steerable wire-guide may have a combined diameter between about 0.018 inches and 0.035 inches. For the steerable wire-guide of this example, the loop is preferably ovoid in shape with a length between approximately 4 millimeters and approximately 5 millimeters, and a width between approximately 2 millimeters and approximately 3 millimeters. The length of such a steerable wire-guide ranges from about 180 centimeters to about 480 centimeters.

Optionally, as shown in the embodiments of FIGS. 5-13B and 33, the steerable wire-guide 10 can further comprise a tubular member 30. In these embodiments, at least a portion of the elongate member 12 may be slidably disposed within tubular member 30. Tubular member 30 may provide support to at least a portion of the elongate member 12. As illustrated in FIGS. 5-13B, tubular member 30 comprises a tubular member proximal end 32 and a tubular member distal end 34. The elongate member 12 may be oriented within the tubular member 30 such that the leading portion 14 extends from the tubular member distal end 34 and the body portion 18, and more specifically the first wire proximal end-portion 27 and the second wire proximal end-portion 29, extends from the tubular member proximal end 32. Tubular member 30 can be formed from polytetrafluoroethylene or other suitable materials know to those of ordinary skill in the medical device arts.

Optionally, as shown in FIGS. 9-17, the steerable wire-guide 10 may further comprise a removable handle 50 detachably associated with the tubular member proximal end 32. The removable handle 50 facilitates the user's ability to manipulate the first and second wires 26, 28. The removable handle 50 further provides the user with the option of retracting the tubular member 30 from the patient leaving the elongate member 12 in position within a patient, thereby permitting the exchange of other medical devices over the elongate member 12. Alternatively, the user is provided with the option of retracting the elongate member 12 from the patient leaving the tubular member 30 in place, thereby permitting the exchange of other wire-guides through the tubular member 30.

Figure 14:
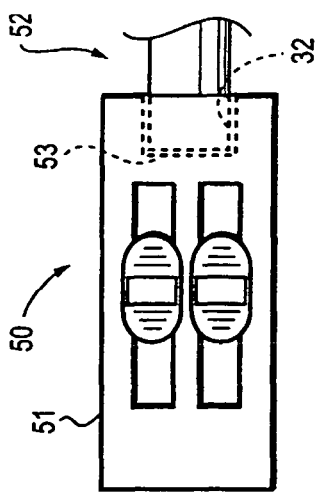
FIG. 14 is a side-view of a releasable connector detachably connecting a gripping portion of a removable handle and a tubular member proximal end according to an embodiment of the invention.

As FIGS. 14-17 show, removable handle 50 comprises a gripping portion 51 and a releasable connector 52 that detachably interconnects the gripping portion 51 and the tubular member proximal end 32. Several embodiments of releasable connector 52 have been contemplated including, but not limited to, an interference fit, a threaded connection and a snap-fit connection. For example, FIGS. 14 and 15 illustrate exemplary embodiments of a releasable connector 52 forming an interference fit connection with the tubular member proximal end 32. In the embodiment shown in FIG. 14, the releasable connector 52 comprises a longitudinal bore 53 into which the tubular member proximal end 32 forms an interference fit. Alternatively, in the embodiment shown in FIG. 15, the releasable connector 52 comprises a protrusion 54 defining an interior lumen through which the proximal portions of the first and second wires extend. Protrusion 54 forms an interference fit within the tubular member proximal end 32.

Figure 16:
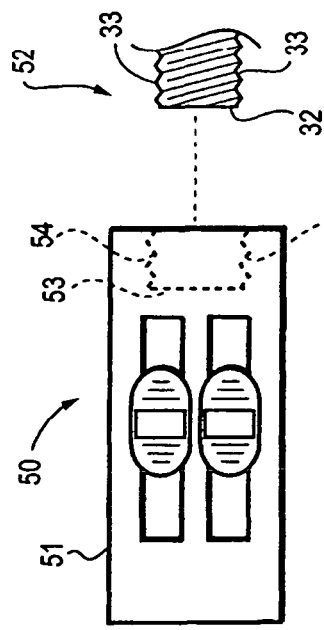
FIG. 16 is a side-view of a releasable connector detachably connecting a gripping portion of a removable handle and a tubular member proximal end according to an alternate embodiment of the invention.

FIG. 16 illustrates a non-limiting exemplary embodiment of a releasable connector 52 that forms a threaded connection with the tubular member proximal end 32. In this embodiment, the releasable connector 52 comprises a longitudinal bore 53 having internal threads 55 and the tubular member proximal end 32 comprises an external threaded portion 33. The removable handle 50 is releasably attached to the tubular member proximal end 32 by threading the external threaded portion 33 of the tubular member proximal end 32 into the longitudinal bore 53 releasable connector 52. Alternatively, but not shown, the releasable connector comprises a protrusion having external threads and the tubular member proximal end comprises an expanded portion having internal threads. Thus, the removable handle is releasably attached to the tubular member proximal end by threading the protrusion of the releasable connector into the expanded portion of the tubular member proximal end.

Figure 17:
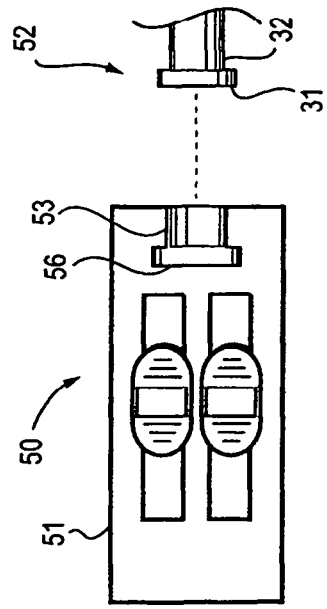
FIG. 17 is a side-view of a releasable connector detachably connecting a gripping portion of a removable handle and a tubular member proximal end according to an alternate embodiment of the invention.

FIG. 17 illustrates a non-limiting exemplary embodiment of a releasable connector 52 that forms a snap-fit connection with the tubular member proximal end 32. In this embodiment, the releasable connector 52 comprises a longitudinal bore 53 having an internal recess 56 and the tubular member proximal end 32 is received therein. The tubular member proximal end 32 comprises a ridge 31 that snaps into the internal recess 56 of the longitudinal bore 53.

Optionally, the removable handle 50 comprises the first wire proximal end-portion 27 and a second wire proximal end-portion 29 mounted for movement as shown in FIGS. 9-13B. Optionally, the removable handle 50 includes a releasable locking mechanism 57 for selectively affixing the first-wire proximal end-portion 27 and/or the second-wire proximal end-portion 29. By way of a non-limiting example, in one embodiment, the releasable locking mechanism 57 comprises a set screw which secures the first-wire proximal end-portion 27 and, optionally, the second-wire proximal end-portion 29 with respect to the removable handle.

Figure 30:
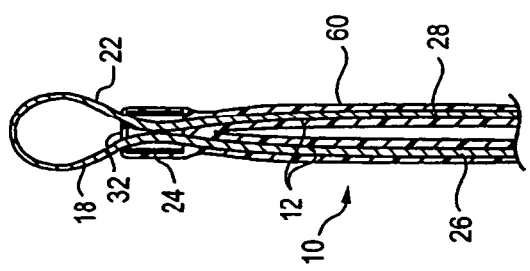
FIG. 30 is a partial, cross-sectional view of a steerable wire-guide comprising a covering according to an alternate embodiment of the invention.

Optionally, the steerable wire-guide 10 can comprise a covering 60 as shown in FIG. 30. Covering 60 can be positioned over the closure member 24 to provide a smooth surface. Optionally, covering 60 can be positioned over the closure member 24 and at least a portion of the leading portion 14. In this case, covering 60 provides a smooth surface between the closure member 24 and the elongate member 12. Alternatively, the covering 60 can be positioned over a portion of, or the entire, elongate member 12 including the loop 22.

The covering 60 can be polytetrafluoroethylene, or any other suitable material. Examples of suitable coverings include, but are not limited to, fluoropolymers, polyurethanes, and other suitable coatings used in the medical device arts. The covering may be applied by various methods known in the art, including dipping, molding, or spraying a suitable coating material. The suitable coating material may include, but is not limited to, polytetrafluoroethylene, urethane, and/or other polymeric coatings directly to the desired portions of the steerable wire-guide. Alternatively, the covering 60 may be applied by heat shrinking a heat shrinkable material about the desired portions of the steerable wire-guide. One preferred heat shrinkable material includes PTFE heat shrinkable material. Heat shrinkable materials facilitate manufacturing while providing a lubricious coating, which facilitates navigation and a reduction in patient trauma. In preferred embodiments, the thickness of the coating is between approximately 0.001 and 0.010 inches. In particularly preferred embodiments, the thickness of the coating is between approximately 0.001 and 0.005 inches. In still more preferred embodiments, the thickness of the coating is between approximately 0.001 and 0.002 inches. These preferred thicknesses provide suitable coatings while not adding significantly to the overall thickness of the device.

Also, the steerable wire-guide 10, with or without the covering 60, may be treated with a hydrophilic coating or hybrid polymer mixture, such as those based on polyvinyl puroladine and cellulose esters in organic solvent solutions. These solutions make the wire-guide particularly lubricious when in contact with body fluids, which aids in navigation.

Radiopaque materials known in the art including, but not limited to, bismuth or gold can be added in the covering 60. Also, radiopaque markers known in the art can be placed on the elongate member 12, the loop 22, and/or the closure member 24. Several examples of suitable radiopaque materials and markers are known in the art, and any suitable material and/or marker can be utilized in the present invention.

Figure 31:
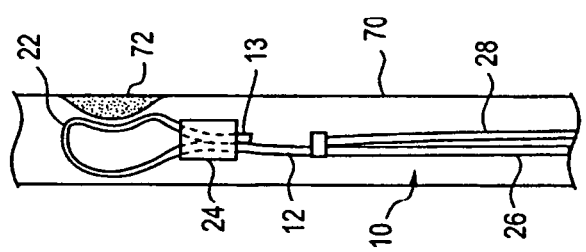
FIG. 31 is a side-view illustrating the steerable wire-guide of FIG. 4 encountering an impediment in a body vessel.

Use of the steerable wire-guide within a body lumen will now be described. FIG. 31 illustrates a steerable wire-guide 10 according to the present invention encountering an impediment 72 within a body vessel 70. As illustrated in the figure, the loop 22 deforms in response to its encounter with the impediment 72. Due to the presence of the loop 22 and closure member 24, the leading portion 14 does not move relative to the remainder of the elongate member 12. Also, the loop 22 deforms in response to the impediment, enabling the steerable wire-guide 10 to continue navigating along the interior of the vessel 70. The resiliency of the loop 22 creates a force opposing the impediment 72 and forces the loop 22 away from the impediment 72, which defines a path for the remainder of the steerable wire-guide 10 to follow.

Figure 32:
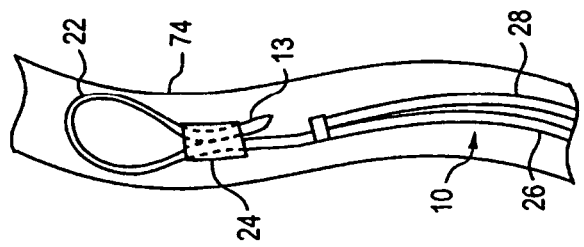
FIG. 32 is a side-view illustrating the steerable wire-guide of FIG. 4 encountering a torturous path within a body vessel.

FIG. 32 illustrates a steerable wire-guide 10 according to the present invention encountering a torturous path 74 within a body vessel. As illustrated in the figure, the loop 22 deforms in response to the torturous path 74. Also, due to the presence of the loop 22 and closure member 24, the distal end 26 does not move relative to the remainder of the elongate member 12.

This allows the wire-guide 10 to continue navigating along the interior of the body vessel.

Figure 33:
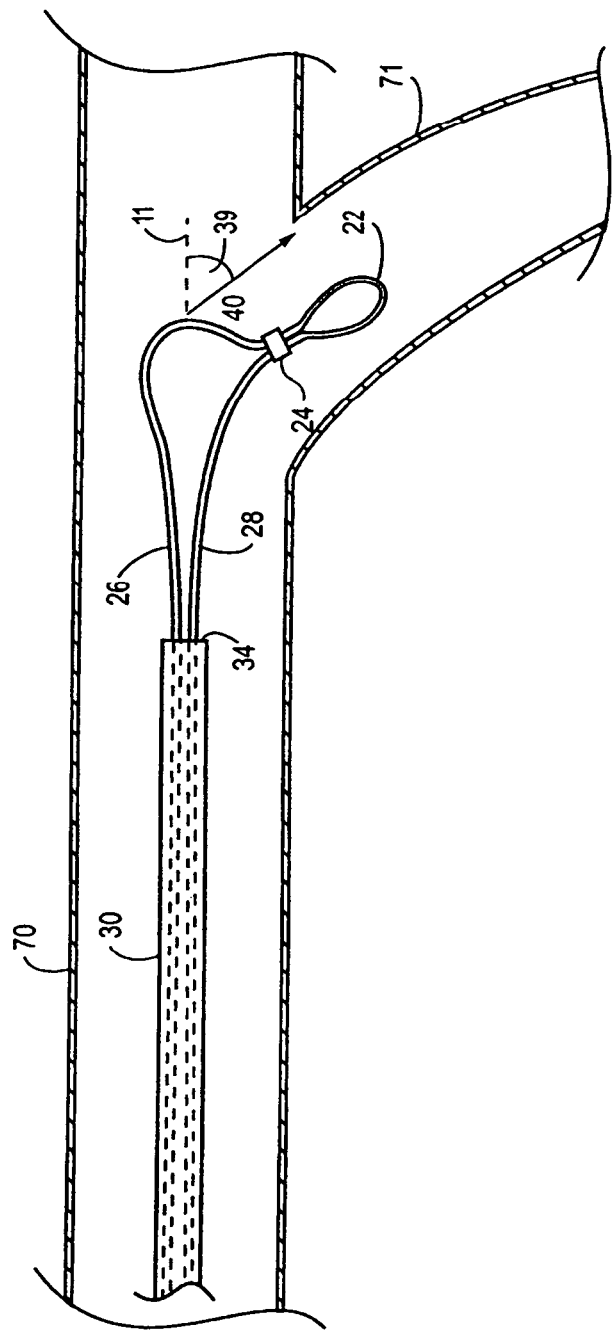
FIG. 33 is a side-view illustrating the steerable wire-guide of FIG. 3 entering a side branch from a main body vessel.

FIG. 33 illustrates a steerable wire-guide 10 according to the present invention entering a branch vessel 71 from a main body vessel 70. As the leading portion 14 approaches the branch vessel 71 from the main vessel 70, the user moves one of the first and second wires 26, 28 relative to the other to bend the leading portion 14 towards the branch vessel 71. With the leading portion 14 aligned with the branch vessel 71, the user then concurrently distally moves the first and second wires 26, 28 to advance the leading portion 14 into the branch vessel 71. Once within the branch vessel 71, the first and second wires 26, 28 can be repositioned to a substantially aligned configuration and the steerable wire-guide 10 can be advanced to the point of treatment.

Although the first and second wires 26, 28 are preferably equal in diameter and length, they may comprise different diameters and lengths. Having the first and second wires 26, 28 with different diameters and lengths facilitates biasing of the steerable wire-guide 15 in a predetermined configuration.

Figure 34:
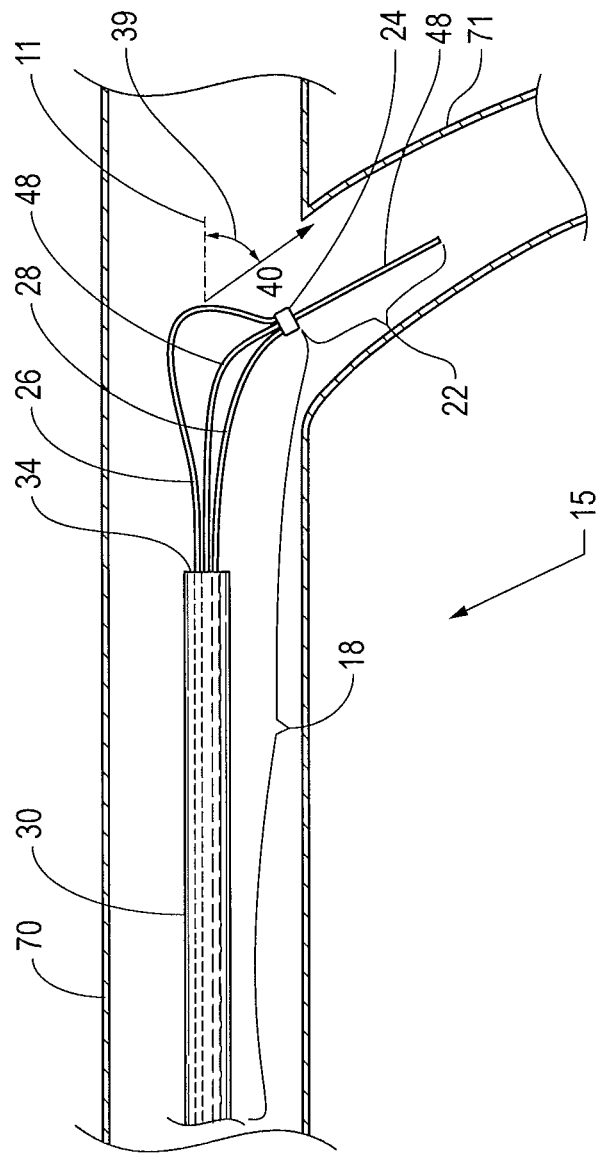
FIG. 34 is a side view illustrating an alternative embodiment of a steerable wire-guide.

Although the embodiments show the leading portion with a loop shaped configuration formed from two wires, other configurations may be used. By way of a non-limiting example, FIG. 34 illustrates a non-loop steerable wire-guide 15 having a body portion 18 with three wires and a leading portion 22 with one of the three wires extending distally beyond closure member 24. In particular, a body portion 18 with a first wire 26, second wire 28, and third wire 48 has at least a portion of the first wire 26, second wire 28, and third wire 48 slidably disposed within a tubular member 30. The three wires 26, 28, 48 are independently controlled, in which each of the three wires 26, 28, 48 can be moved relative to the other two wires. Movement of each of the three wires 26, 28, 48 relative to each other causes the wires 26, 28, 48 to move in a predetermined direction. As FIG. 34 shows, relative distal movement of the third wire 48 with respect to the second wire 28 and relative distal movement of the the first wire 26 with respect to the third wire 48 directs the leading portion 22 in a first direction 40, at an angle 39 relative to the longitudinal axis 11. Other non-loop configurations with a body portion utilizing multiple wires are contemplated.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A steerable wire-guide for guiding an elongate medical device through a body lumen of a patient comprising: an elongate member having a longitudinal axis, the elongate member comprising a leading portion and a body portion, the body portion comprising a first wire and a second wire, the first wire and the second wire being moveable relative to each other such that relative distal movement of the first wire with respect to the second wire directs the leading portion in a first direction at an angle relative to the longitudinal axis, and relative distal movement of the second wire with respect to the first wire directs the leading portion in a second direction different from the first direction, and further wherein the body portion further comprises a third wire, the third wire being movable relative to the first and second wires such that movement of the third wire with respect to the first and the second wires causes the leading portion to move in a predetermined third direction, the predetermined third direction being different from the first and second directions, wherein each of the first, the second, and the third wires converge at a single location, and wherein leading portion comprises a distal portion of the third wire that extends distally beyond a distal terminus of the first and second wires.

* * * * *